(12) United States Patent
Watabe et al.

(10) Patent No.: US 8,968,263 B2
(45) Date of Patent: Mar. 3, 2015

(54) ABSORBENT ARTICLE

(75) Inventors: Yoshihisa Watabe, Kagawa (JP);
Hirotomo Mukai, Kagawa (JP);
Natsuko Takahashi, Kagawa (JP);
Tomoko Tsuji, Kagawa (JP)

(73) Assignee: Unicharm Corporation, Ehime-ken (JP)

( * ) Notice: Subject to any disclaimer, the term of this patent is extended or adjusted under 35 U.S.C. 154(b) by 289 days.

(21) Appl. No.: 13/517,060

(22) PCT Filed: Dec. 28, 2010

(86) PCT No.: PCT/JP2010/073790
§ 371 (c)(1),
(2), (4) Date: Jul. 23, 2012

(87) PCT Pub. No.: WO2011/081206
PCT Pub. Date: Jul. 7, 2011

(65) Prior Publication Data
US 2012/0289923 A1 Nov. 15, 2012

(30) Foreign Application Priority Data
Dec. 28, 2009 (JP) .................. 2009-298972

(51) Int. Cl.
*A61F 13/15* (2006.01)
*A61F 13/49* (2006.01)
(Continued)

(52) U.S. Cl.
CPC ....... *A61F 13/49001* (2013.01); *A61F 13/4755* (2013.01); *A61F 13/53409* (2013.01);
(Continued)

(58) Field of Classification Search
CPC .............. A61F 13/475; A61F 13/4751; A61F 13/4755; A61F 13/49001; A61F 13/494; A61F 13/49406; A61F 13/49426; A61F 13/4946; A61F 13/53409; A61F 13/53418; A61F 2013/530883; A61F 2013/530927; A61F 2013/530934; A61F 2013/530941; A61F 2013/530948
USPC .................................. 604/385.101, 385.201
See application file for complete search history.

(56) References Cited

U.S. PATENT DOCUMENTS 2,852,026 A * 9/1958 Karr .............................. 604/377
4,381,782 A * 5/1983 Mazurak et al. ............... 604/368
(Continued)

FOREIGN PATENT DOCUMENTS

CN 101547669 A 9/2009
EP 0336826 A1 10/1989
(Continued)

OTHER PUBLICATIONS

Office Action mailed Feb. 21, 2014, corresponds to Chinese patent application No. 201080059660.7.
(Continued)

*Primary Examiner* — Lynne Anderson
(74) *Attorney, Agent, or Firm* — Lowe Hauptman & Ham LLP

(57) ABSTRACT

An absorbent article according to the present invention includes a topsheet, a backsheet, and an absorber. The absorber has a body unit having a foreside constricted portion and a backside constricted portion, and a pair of extension units extending outside in the widthwise direction of the absorber from the body unit. An outer region is folded toward an inner region at the side of the topsheet, and the maximum length of the inner region along the longitudinal direction of the absorber is shorter than the maximum length of the outer region.

10 Claims, 9 Drawing Sheets

(51) Int. Cl.
*A61F 13/475* (2006.01)
*A61F 13/534* (2006.01)
*A61F 13/494* (2006.01)
*A61F 13/53* (2006.01)
*A61F 13/45* (2006.01)

(52) U.S. Cl.
CPC ..... *A61F13/15699* (2013.01); *A61F 13/49426* (2013.01); *A61F 13/53418* (2013.01); *A61F 13/15747* (2013.01); *A61F 2013/530437* (2013.01); *A61F 2013/530875* (2013.01); *A61F 2013/530883* (2013.01); *A61F 2013/455* (2013.01); *A61F 2013/4568* (2013.01); *A61F 2013/4581* (2013.01)
USPC .............................. 604/385.101; 604/385.201

(56) References Cited

U.S. PATENT DOCUMENTS

| | | | | |
|---|---|---|---|---|
| 4,410,324 | A | * | 10/1983 | Sabee .......................... 604/368 |
| 5,318,553 | A | * | 6/1994 | Weeks et al. ................. 604/378 |
| 5,776,121 | A | * | 7/1998 | Roe et al. ................. 604/385.25 |
| 5,792,130 | A | | 8/1998 | Widlund et al. |
| 7,378,566 | B2 | * | 5/2008 | Soerens et al. ................ 604/365 |
| 8,361,047 | B2 | | 1/2013 | Mukai et al. |
| 2004/0210204 | A1 | | 10/2004 | Shimada et al. |
| 2008/0140042 | A1 | | 6/2008 | Mukai et al. |
| 2010/0324521 | A1 | | 12/2010 | Mukai et al. |
| 2010/0324523 | A1 | | 12/2010 | Mukai et al. |

FOREIGN PATENT DOCUMENTS

| | | | |
|---|---|---|---|
| FR | 2629688 | A1 | 10/1989 |
| JP | 51138233 | U | 11/1976 |
| JP | 57082502 | A | 5/1982 |
| JP | 58012652 | A | 1/1983 |
| JP | 60158827 | U | 10/1985 |
| JP | 2011141 | A | 1/1990 |
| JP | 3123553 | A | 5/1991 |
| JP | 6169950 | A | 6/1994 |
| JP | 9506527 | A | 6/1997 |
| JP | 2004313601 | A | 11/2004 |
| JP | 2007050024 | A | 3/2007 |
| WO | 9948454 | A1 | 9/1999 |
| WO | 2008069279 | A1 | 6/2008 |

OTHER PUBLICATIONS

Office Action mailed Jul. 23, 2013 corresponds to Japanese patent application No. 2009-298972.
Extended European Search Report issued Jul. 1, 2013 corresponds to EP Patent application No. 10841061.4.
International Search Report and Written Opinion for PCT/JP2010/073790, dated Apr. 5, 2011.

* cited by examiner (a)

(b)

ABSORBENT ARTICLE

RELATED APPLICATIONS

The present application is a National Phase of International Application Number PCT/JP2010/073790, filed Dec. 28, 2010, and claims priority from Japanese Application Number 2009-298972, filed Dec. 28, 2009.

TECHNICAL FILED

The present invention relates to an absorbent article which is provided with: a liquid-permeable topsheet; a liquid-impermeable backsheet; and an absorber which is provided between the topsheet and the backsheet.

BACKGROUND ART

In an absorbent article such as a disposable diaper, an inside leg region facing a crotch of a wearer is sandwiched by the femoral region of the wearer. Therefore, in order to ensure good fitting feeling to the crotch of the inside leg region even when the wearer has moved, an absorber generally has a planar shape in which a center of the absorber is constricted as with a sand clock. That is, a width of the absorber is narrowest in the inside leg region positioned at a center portion in the longitudinal direction of the absorbent article, and is widened in an outer region more than the inside leg region.

However, in a disposable diaper provided with the absorber having such a shape, since an effective absorption area of the absorber is reduced in the inside leg region near an excretion position of urine or the like, there is a problem that the absorber may not sufficiently absorb the urine or the like. Of course, if the width of the inside leg region is increased, absorption performance is improved. However, the fitting feeling to a wearer may be deteriorated. Therefore, in order to cope with such a problem, there has been disclosed an absorbent article having an absorber provided at both sides thereof with auxiliary absorbers erected toward a wearer (refer to Patent Document 1, for example).

According to the absorbent article, while the absorber is absorbing bodily waste such as urine, it is possible for the auxiliary absorbers to block the bodily waste because the auxiliary absorbers are erected. That is, it is possible to ensure good fitting feeling to a wearer and prevent the bodily waste from leaking to the outside of the absorbent article (so called side leakage).

PRIOR ART DOCUMENT

Patent Document

[Patent Document 1]: Japanese Patent Application Publication No. 3-123553 (Pages 2 to 3, FIG. 1 and FIG. 4)

SUMMARY OF THE INVENTION

However, in the above-mentioned conventional absorbent article, when a lot of urine or the like is excreted in a short period of time or when watery stools, loose stools or the like difficult to be absorbed are excreted, the bodily waste may still flow over the auxiliary absorbers, resulting in the occurrence of side leakage.

Therefore, it is an object of the present invention to provide an absorbent article which is capable of ensuring good fitting feeling to a wearer and preventing side leakage of bodily waste more reliably.

To solve the above-mentioned problem, the feature of the present invention is an absorbent article (absorbent article 1), comprising: a topsheet (topsheet 10) which is provided at a side coming into contact with a skin of a wearer; a backsheet (backsheet 20) which is provided at a side separated from the wearer; and an absorber (absorber 30) which is provided between the topsheet and the backsheet, wherein both side portions (both side portions 30E) in a widthwise direction of the absorber are folded, wherein the absorber comprises: a body unit (body unit 310) having a constricted portion (foreside constricted portion 312A, backside constricted portion 312B) constricted inside in the widthwise direction when viewed from a plan view of the absorber; and a pair of extension units (extension unit 320) which extends from the body unit to the outside in the widthwise direction of the absorber in a state in which the both side portions have been unfolded, wherein the constricted portion is formed in a center region in a longitudinal direction of the absorber, and wherein the extension unit comprises: an inner region (inner region 321) which is provided at the constricted portion and is continuous to the body unit; and an outer region (outer region 322) which is continuous to the inner region and is positioned outside of the inner region in the widthwise direction of the absorber, and wherein the outer region is folded toward the inner region at a side of the topsheet, and a length of the inner region along the longitudinal direction of the absorber (maximum length L321) is shorter than a length of the outer region along the longitudinal direction (maximum length L322).

BRIEF DESCRIPTION OF THE DRAWINGS

FIG. 4 (b) is a plan view of the absorber 30 according to the embodiment of the present invention (after the outer region 322 is folded).

EMBODIMENTS FOR CARRYING OUT THE INVENTION

Figure 1:
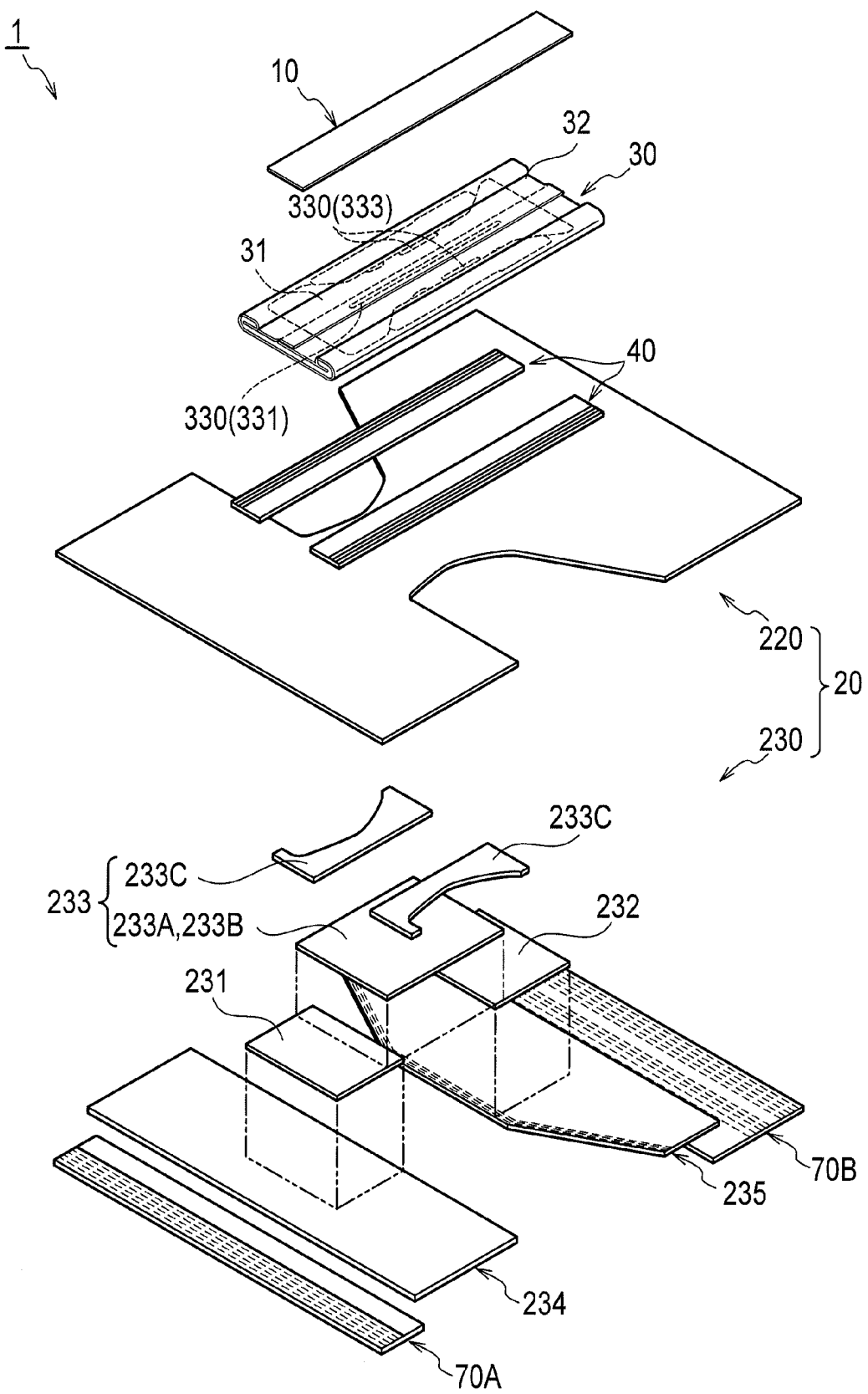
FIG. 1 is an exploded perspective view of an absorbent article 1 according to an embodiment of the present invention.

An embodiment of an absorbent article according to the present invention is explained with reference to the drawings. In the following description of the drawings, the same or similar reference numerals are used to designate the same or similar parts. It will be appreciated that the drawings are schematically shown and the ratio and the like of each dimension are different from the real ones. Therefore, a specific dimension should be determined in view of the following description. Moreover, among the drawings, the respective dimensional relations or ratios may differ.

(Configuration of Absorbent Article)

Figure 2:
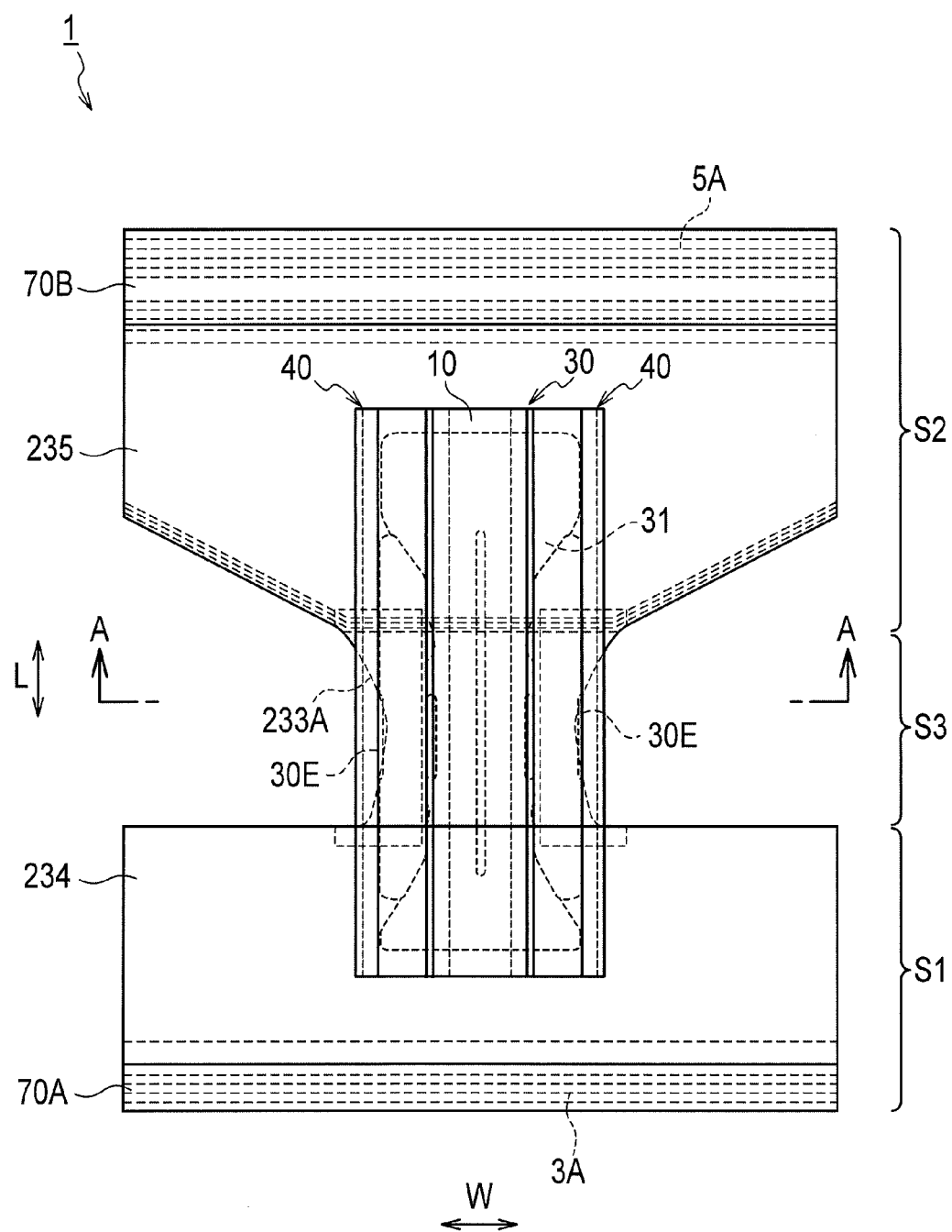
FIG. 2 is a plan view of the absorbent article 1 according to the embodiment of the present invention.
Figure 3:
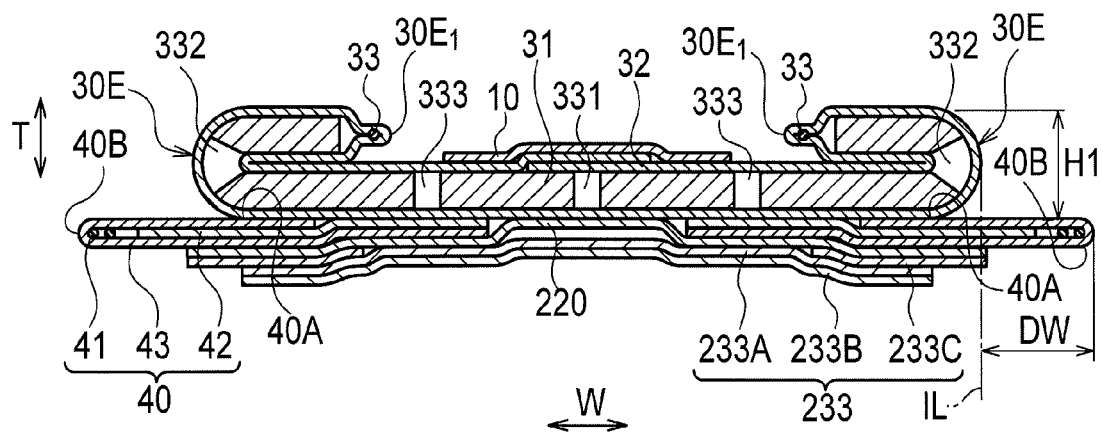
FIG. 3 (a) and FIG. 3 (b) are sectional views of the absorbent article 1 according to the embodiment of the present invention, which are taken along line A-A of FIG. 2.
Figure 3:
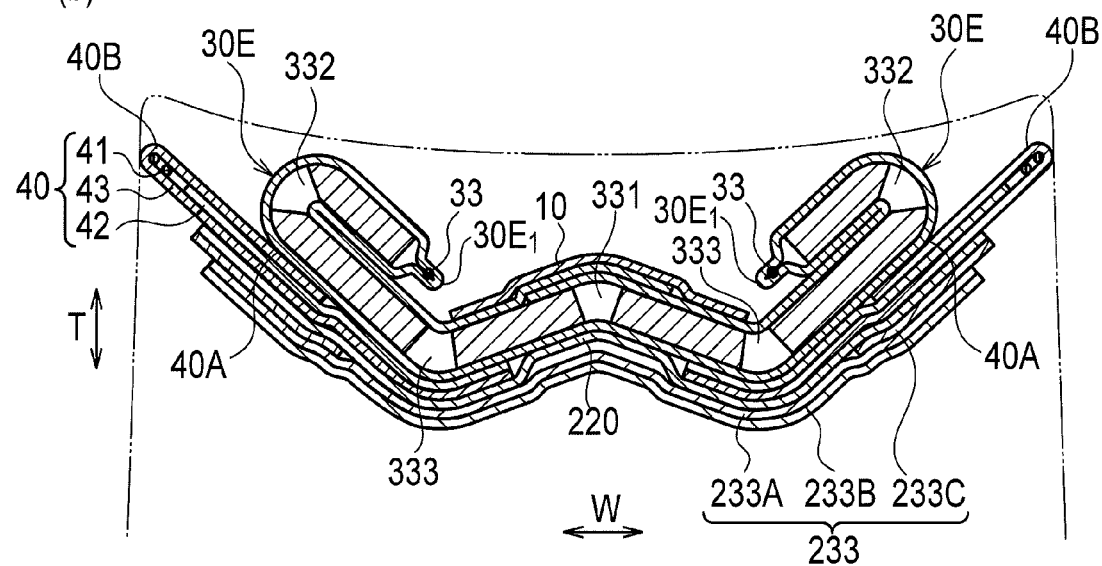

First of all, the configuration of an absorbent article 1 according to the present embodiment is explained with reference to the drawings. FIG. 1 is an exploded perspective view of the absorbent article 1. FIG. 2 is a plan view of the absorbent article 1. FIG. 3 is a sectional view of the absorbent article 1, which is taken along line A-A of FIG. 2. In addition, the absorbent article 1 according to the present embodiment is a disposable diaper.

As illustrated in FIG. 1 to FIG. 3, the absorbent article 1 has a longitudinally elongated shape in the front and rear direction from the abdomen to the back of a wearer. The absorbent article 1 has a front waistline region S1 corresponding to the front waistline of the wearer, a rear waistline region S2 corresponding to the rear waistline of the wearer, and a crotch region S3 corresponding to the crotch of the wearer between the front waistline region S1 and the rear waistline region S2, in the longitudinal direction L of the absorbent article 1.

The absorbent article 1 is mainly comprised of a topsheet 10, a backsheet 20, an absorber 30, and leakage preventing units 40.

The topsheet 10 is provided at a side coming into contact with a skin of the wearer. As the topsheet 10, a liquid-permeable sheet, such as nonwoven fabric or plastic film having apertures, which allows fluid to pass therethrough, is used.

The backsheet 20 is provided at a side separated from the wearer. The backsheet 20 is comprised of an exterior topsheet 220 and an exterior sheet 230. The exterior topsheet 220 is provided between the absorber 30 and the exterior sheet 230. Furthermore, the exterior topsheet 220 is provided in the front waistline region S1, the rear waistline region S2, and the crotch region S3. As the exterior topsheet 220, a sheet such as nonwoven fabric is used.

The exterior sheet 230 is provided outside (the side separated from the wearer) of the exterior topsheet 220. The exterior sheet 230 is comprised of a foreside exterior sheet 231, a backside exterior sheet 232, a crotch exterior sheet 233, a front waistline exterior sheet 234, and a rear waistline exterior sheet 235.

The foreside exterior sheet 231 is provided in the front waistline region S1. As the foreside exterior sheet 231, a water-proof film (for example, polyethylene) or the like are used.

The backside exterior sheet 232 is provided in the rear waistline region S2. The backside exterior sheet 232 is formed of a liquid-impermeable sheet such as a water-proof film.

The crotch exterior sheet 233 is provided in the crotch region S3. The crotch exterior sheet 233 is comprised of a liquid-impermeable crotch inner sheet 233A such as a water-proof film, a crotch outer layer sheet 233B such as nonwoven fabric provided at a position separated from the wearer with respect to the crotch inner sheet 233A, and a crotch sheet 233C, such as nonwoven fabric, provided between the exterior topsheet 220 and the crotch inner sheet 233A.

The foreside exterior sheet 231 is bonded with the front waistline exterior sheet 234. As the front waistline exterior sheet 234, a stretchable sheet is used. A foreside waist sheet 70A formed of nonwoven fabric is bonded with the front waistline exterior sheet 234. The foreside waist sheet 70A surrounds an elongated waist elastic member 3A, such as synthetic rubber, which is stretchable in a widthwise direction W perpendicular to the longitudinal direction L of the absorbent article 1.

The backside exterior sheet 232 adheres to the rear waistline exterior sheet 235. As the rear waistline exterior sheet 235, a stretchable sheet is used. A backside waist sheet 70B formed of nonwoven fabric is bonded with the rear waistline exterior sheet 235. The backside waist sheet 70B surrounds an elongated waist elastic member 5A, such as synthetic rubber, which is stretchable in the widthwise direction W of the absorbent article 1.

The absorber 30 is provided between the topsheet 10 and the backsheet 20 (the exterior topsheet 220) to absorb bodily waste of the wearer. The absorber 30 is comprised of an absorber core 31 and covering members 32.

The absorber core 31 absorbs the bodily waste of the wearer. As the absorber core 31, a mixture of ground pulp and high absorbent polymer particle, or the like are used. The absorber 30, specifically, the absorber core 31 is covered with the covering members 32 (sheet-like members). The covering member 32 is formed of hydrophilic nonwoven fabric or the like.

The leakage preventing units 40 are provided at both side portions 30E (around second bending facilitation portions 332 of FIG. 3) in the widthwise direction W of the absorber 30 in the state in which extension units 320 have been folded toward a body unit 310. The leakage preventing unit 40 is comprised of a plurality of strand-shaped rubbers 41 (leakage preventing elastic members), leakage preventing films 42, and a leakage preventing sheet 43.

The strand-shaped rubbers 41 are provided along the longitudinal direction L of the absorbent article 1. The strand-shaped rubbers 41 are covered with the leakage preventing sheet 43 in an stretched state and are fixed to the leakage preventing sheet 43. As the strand-shaped rubbers 41, synthetic rubbers or the like stretchable along the longitudinal direction L are used. The leakage preventing film 42 is provided inside in the widthwise direction W of the absorbent article 1 more than the strand-shaped rubbers 41. As the leakage preventing film 42, a liquid-impermeable sheet such as a water-proof film (for example, polyethylene) is used. The leakage preventing sheet 43 surrounds a part of the strand-shaped rubbers 41 and the leakage preventing film 42. As the leakage preventing sheet 43, a sheet such as nonwoven fabric is used.

The leakage preventing unit 40 as described above has a bonding end 40A and a free end 40B. The bonding end 40A is formed along the longitudinal direction L of the absorbent article 1 and is bonded with the both side portions 30E of the absorber 30. The bonding end 40A is positioned inside in the widthwise direction W of the absorber 30 with respect to a folding line IL which will be described later. Meanwhile, the free end 40B is formed along the longitudinal direction L of the absorbent article 1 and serves as the other end of the bonding end 40A. The free end 40B rises up from the absorbent article 1 at the time of the wearing of the absorbent article 1, and comes into contact with the skin of the wearer. The free end 40B is positioned outside in the widthwise direction W of the absorber 30 with respect to the lower side of the absorber 30 and the folding line IL in the state in which the extension units 320 have been folded toward the body unit 310.

(Structure of Absorber)

Next, the structure of the absorber 30 will be described with reference to the drawings.

Figure 4:
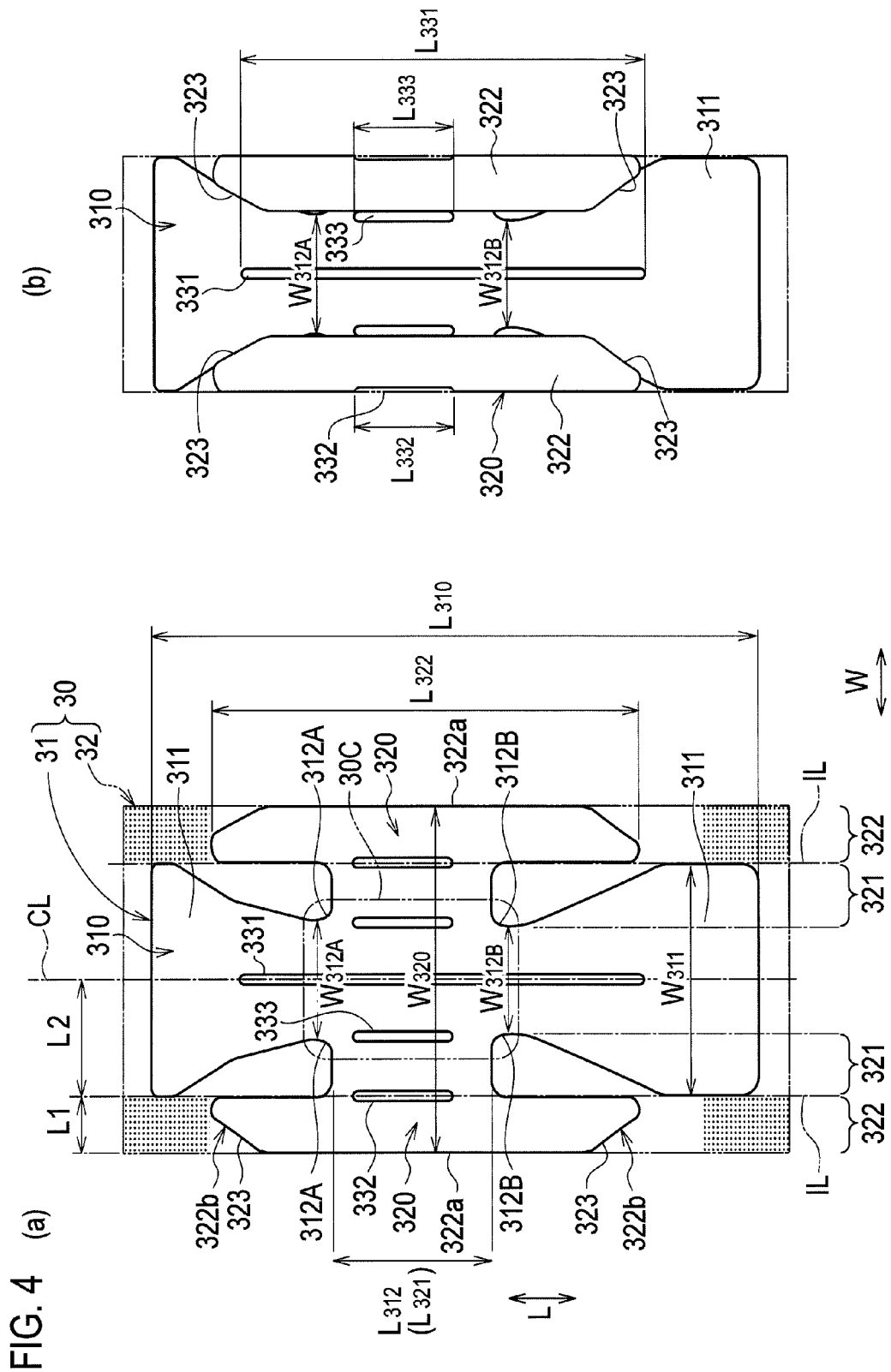
FIG. 4 (a) is a plan view of an absorber 30 according to the embodiment of the present invention (before an outer region 322 is folded).

FIG. 4 (*a*) is a plan view of the absorber 30 (before an outer region 322 is folded). FIG. 4 (*b*) is a plan view of the absorber 30 (after the outer region 322 is folded).

As illustrated in FIG. 4, the absorber core 31 constituting the absorber 30 has the body unit 310 and the extension units 320. The body unit 310 forms the body of the absorber 30. The body unit 310 has wide portions 311 and a plurality of constricted portions 312.

The wide portion 311 is positioned in a pair of waistline regions (the front waistline region S1 and the rear waistline region S2) and has a wider width along the widthwise direction W of the absorber 30 than the constricted portions 312.

The constricted portions 312 are constricted inside in the widthwise direction W of the absorber 30 when viewed from the plan view of the absorber 30. The constricted portions 312 have a width gradually reduced from the wide portion 311 along the widthwise direction W of the absorber 30, and are continuous to the extension units 320.

The constricted portion 312 is comprised of a pair of foreside constricted portions 312A positioned at the side of the front waistline region S1, and a pair of backside constricted portions 312B positioned at the side of the rear waistline region S2. An interval W312A between the pair of foreside constricted portions 312A and an interval W312B between the pair of backside constricted portions 312B are narrower than the width along the widthwise direction W of the wide portion 311. In the present embodiment, the interval W312A between the pair of foreside constricted portions 312A is wider than the interval W312B between the pair of backside constricted portions 312B.

The extension unit 320 is provided in the form of a pair on left and right sides. Each of the extension units 320 extends from the body unit 310 to the outside in the widthwise direction W of the absorber 30 in a center region 30C in the longitudinal direction L of the absorber 30. In addition, the center region 30C is not limited to a region illustrated in FIG. 4 (a). For example, the center region 30C may be a center region of regions obtained by dividing the absorber 30 into three in the longitudinal direction L. A width W320 of the absorber 30 from an outer edge 322a of one extension unit 320 to an outer edge 322a of the other extension unit 320 is wider than an end portion in the longitudinal direction L, specifically, a width W311 of the absorber 30 in the wide portion 311 in the state in which the both side portions 30E have been unfolded.

The extension units 320 are folded toward the body unit 310 at the side of the topsheet 10 along the folding line IL extending in the longitudinal direction L of the absorber 30. A length L1 along the widthwise direction W of the absorber 30 from the outer edge 322a to the folding line IL is equal to or less than a length L2 along the widthwise direction W of the absorber 30 from a center line CL, which passes through the center in the widthwise direction W of the body unit 310, to the folding line IL. In the present embodiment, the folding line IL is positioned at the boundary between an inner region 321 and an outer region 322.

In the state in which the extension units 320 have been folded toward the body unit 310, end portions in the longitudinal direction L with respect to both end portions 322b of the outer region 322 are bonded with the body unit 310 through the covering members 32. That is, a part of the covering member 32 positioned outside of the outer region 322 in the longitudinal direction L is bonded with the body unit 310. In the present embodiment, adhesive (hot-melt adhesive) is coated on corners (dotted portions of FIG. 4 (a)) of the covering members 32. In this way, in the state in which the extension units 320 have been folded toward the body unit 310, the outer regions 322 are held on the body unit 310.

More specifically, the extension unit 320 has the inner region 321 and the outer region 322. The inner region 321 is positioned at the side closer to the body unit 310 than the folding line IL is and is continuous to the body unit 310. The outer region 322 is positioned outside of the folding line IL in the widthwise direction W of the absorber 30 in the extension units 320. The outer region 322 is folded along the folding line IL together with the covering member 32.

The maximum length L322 of the outer region 322 along the longitudinal direction L is longer than an interval L312 between the constricted portions 312 adjacent in the longitudinal direction L and the maximum length L321 of the inner region 321 along the longitudinal direction L. Furthermore, the maximum length L322 of the outer region 322 is shorter than the maximum length L310 along the longitudinal direction L of the body unit 310.

The both end portions 322b in the longitudinal direction L of the outer region 322 are formed with cutout portions 323. The cutout portion 323 is formed by cutting the side of the outer edge 322a of the outer region 322 when viewed from the plan view of the absorber 30. The both end portions 322b of the outer region 322 are tapered as moving toward outside in the longitudinal direction L. Preferably, the shape of the both end portions 322b corresponds to the shape from the wide portion 311 to the constricted portion 312 in the state in which the extension units 320 have been folded toward the body unit 310.

In this way, when the extension units 320 have been folded toward the side of the body unit 310, since the absorber 30 is thickened in a crotch portion at which the inner region 321 and the outer region 322 overlap with each other in the thickness direction, a leakage preventing effect is increased. Moreover, it is possible to relatively reduce the thickness of the absorber 30 at an end portion (at the side of the wide portion 311) in the longitudinal direction L of the absorber 30, at which the inner region 321 and the outer region 322 do not overlap with each other. Consequently, at the time of the wearing of the absorbent article 1, it is possible to increase the absorption capacity of the crotch portion, and to make the external appearance of a front and rear portion outside in the longitudinal direction more slimmed-down than the crotch portion.

The absorber 30 is formed with bending facilitation units 330 which are processed to allow the extension units 320 to be bent easily along the folding line IL or a straight line parallel to the folding line IL. The bending facilitation unit 330 has a first bending facilitation portion 331, a pair of second bending facilitation portions 332, and a pair of third bending facilitation portions 333. In the present embodiment, the first bending facilitation portion 331, the second bending facilitation portions 332, and the third bending facilitation portions 333 are slits formed in the absorber 30.

The first bending facilitation portion 331 is formed along the center line CL. The first bending facilitation portion 331 extends from one wide portion 311 to the other wide portion 311.

The second bending facilitation portions 332 are formed along the longitudinal direction L. The second bending facilitation portions 332 are positioned outside of the first bending facilitation portion 331 in the widthwise direction W of the absorber 30.

Specifically, the second bending facilitation portion 332 is positioned at the boundary between the inner region 321 and the outer region 322. A length L332 of the second bending facilitation portion 332 is shorter than a length L331 of the first bending facilitation portion 331. Furthermore, the first bending facilitation portion 331 and the second bending facilitation portions 332 are formed at positions corresponding to the extension units 320 in the longitudinal direction L. That is, the first bending facilitation portion 331 and the second bending facilitation portions 332 are formed in the area, in which the extension units 320 is provided, in the longitudinal direction L in order to facilitate the bending of the extension units 320.

The third bending facilitation portion 333 is formed along the longitudinal direction L of the absorber 30. The third bending facilitation portion 333 is positioned between the first bending facilitation portion 331 and the second bending facilitation portion 332. Specifically, the third bending facilitation portion 333 is positioned at the boundary between the body unit 310 and the inner region 321. A length L333 of the third bending facilitation portion 333 is approximately the same as the length L332 of the second bending facilitation portion 332.

Furthermore, before the extension units 320 are folded toward the body unit 310 (before the outer region 322 is folded), a pair of strand-shaped rubbers 33 (elastic members) installed along the longitudinal direction L of the absorber 30 is provided at tip portions 30E1 positioned outermost in the widthwise direction W of the absorber 30 at both side portions 30E of the absorber 30 (see FIG. 3). As the strand-shaped rubbers 33, synthetic rubbers which are stretchable along the longitudinal direction L of the absorber 30 are used.

The strand-shaped rubbers 33 are fixed inside the absorber 30 in a stretched state along the longitudinal direction L of the absorber 30. That is, the strand-shaped rubbers 33 are covered with the covering members 32 together with the absorber core 31.

In the state in which the extension units 320 have been folded toward the body unit 310, it is preferable that a distance DW from the folding line IL to the free end 40B of the leakage preventing unit 40 is larger than a height H1 from the exterior topsheet 220 along a thickness direction T of the absorbent article 1 to the extension units 320 (see FIG. 3 (a)).

(Manufacturing Method of Absorbent Article)

Next, a manufacturing method of the absorbent article for manufacturing the above-mentioned absorber 30 will be described with reference to the drawings.

Figure 5:
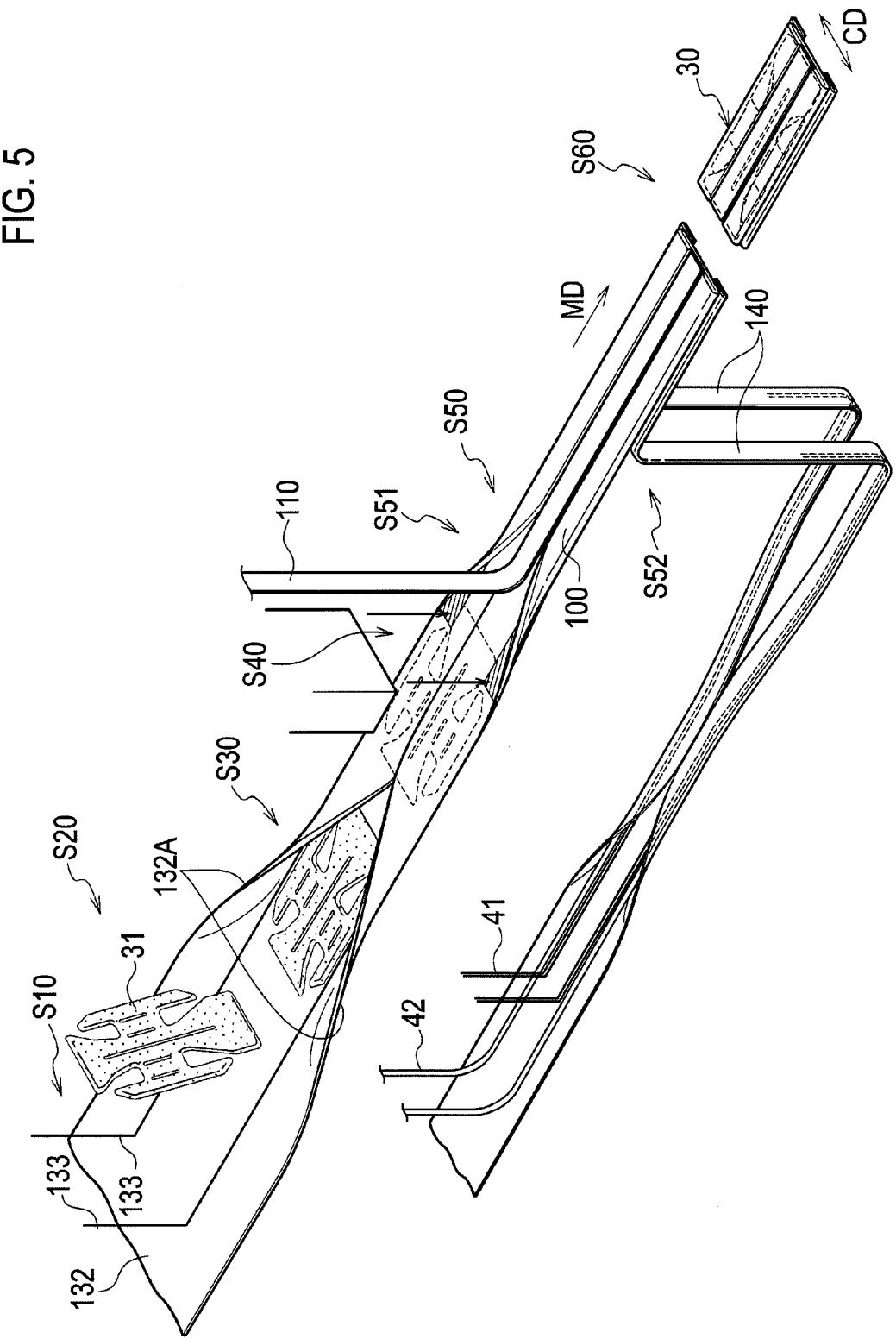
FIG. 5 is a diagram explaining a manufacturing method of the absorbent article according to the embodiment of the present invention.

FIG. 5 is a diagram explaining a manufacturing method of the absorbent article according to the present embodiment. In addition, in FIG. 5, in addition to an adhesive coating step S40 which will be described later, a step of coating members constituting the absorbent article 1 using adhesive (for example, hot-melt adhesive) is omitted.

The manufacturing method of the absorbent article includes a rubber bonding step S10, a core stacking step S20, a core covering step S30, an adhesive coating step S40, an absorber folding step S50, and an absorber cutting step S60.

In the rubber bonding step S10, a rubber continuous body 133 having the pair of continuous strand-shaped rubbers 33 is bonded with a covering member web 132 having the continuous covering members 32 conveyed along a machine direction MD. Specifically, the pair of rubber continuous bodies 133 is bonded with the outside (a position corresponding to the tip portion 30E1) of the absorber core 31 to be arranged on the covering member web 132.

In the core stacking step S20, the absorber core 31 having the above-mentioned body unit 310 and extension unit 320 is stacked on the covering member web 132 to which the pair of rubber continuous bodies 133 has been bonded. Specifically, the absorber core 31 is stacked between the pair of rubber continuous bodies 133 bonded with the covering member web 132.

In addition, the absorber core 31 is provided with the body unit 310 (the wide portions 311 and the constricted portions 312), the extension units 320 (the inner region 321 and the outer region 322), the bending facilitation units 330 or the like through a core stacking apparatus (not illustrated).

In the core covering step S30, both end portions 132A of the covering member web 132, to which the absorber core 31 and the pair of strand-shaped rubbers 33 have been bonded, is folded to surround the absorber core 31 and the pair of strand-shaped rubbers 33, so that the absorber core 31 and the pair of strand-shaped rubbers 33 are covered with the covering member web 132. At this time, the absorber core 31 is covered with the covering member web 132 in the state in which the extension unit 320 has not been folded toward the body unit 310 and has extended from the body unit 310.

In the adhesive coating step S40, the adhesive (the hot-melt adhesive) is coated at a position corresponding to the corners (the dotted portions of FIG. 4 (a)) of the covering members 32. In addition, in the adhesive coating step S40, the adhesive may not be coated only on the covering member 32 corresponding to the corners of the covering members 32. For example, the adhesive may be coated on the covering member 32 corresponding to the whole of the outer region 322, or may be coated on the covering member 32 corresponding to only the both end portions 322b of the outer region 322.

In the absorber folding step S50, the extension units 320 are folded toward the body unit 310 along the folding line IL. In this way, the extension units 320 are bonded with the body unit 310, so that a product continuous body 100 is formed.

In the absorber cutting step S60, the product continuous body 100 is cut along a crossing direction CD perpendicular to the machine direction MD to have a size corresponding to the absorber 30 of each absorbent article 1. In this way, the absorber 30 corresponding to each absorbent article 1 is completed.

Here, between the adhesive coating step S40 and the absorber cutting step S60, a step S51 of adhering a topsheet web 110 having the continuous topsheet 10 to the product continuous body 100, and a step S52 of adhering a leakage preventing unit web 140 to the lower surface side of the product continuous body 100, may also be performed, wherein the leakage preventing unit web 140 has the continuous strand-shaped rubbers 41 and leakage preventing films 42 constituting the leakage preventing unit 40. A member positioned inside of the backsheet 20, that is, at the side of the skin of a wearer, is formed, and the absorber 30 adheres to the backsheet 20 provided with the member in advance, so that each absorbent article 1 is formed.

In the above-mentioned present embodiment, the extension units 320 are provided at the constricted portions (the foreside constricted portions 312A and the backside constricted portions 312B) of the absorber 30, which are constricted inside in the widthwise direction W. Furthermore, the maximum length L321 of the inner region 321 of the extension unit 320 is shorter than the maximum length L322 of the outer region 322. That is, since the extension unit 320 is continuous to the body unit 310 by the inner region 321 having a short length, it is possible to easily trace the movement of the crotch of a wearer and to ensure good fitting feeling to the wearer.

Moreover, in the present embodiment, since the outer region 322 having a long length is provided in the center region 30C in the longitudinal direction of the absorber 30, that is, provided around an excretion portion of a wearer, it is possible to improve the absorption performance of bodily waste and to reliably prevent side leakage of the bodily waste.

In the present embodiment, since the length L1 from the outer edge 322a to the folding line IL is equal to or less than the length L2 from the center line CL to the folding line IL, the extension units 320 do not cover the body unit 310. Thus, even when a lot of urine or the like is excreted in a short period of time or when watery stools, loose stools or the like difficult to be absorbed are excreted, the bodily waste is absorbed by the body unit 310 once and the absorbed bodily waste is diffused to the extension units 320. Specifically, the bodily waste absorbed by the body unit 310 can be diffused to the outer region 322 via the inner region 321 or can be directly diffused to the outer region 322. As a consequence, it is possible for the extension units 320 to prevent side leakage of the bodily waste more reliably.

In the present embodiment, a part (the dotted portion of FIG. 4 (a)) of the covering member 32 positioned outside in the longitudinal direction of the outer region 322 is bonded with the body unit 310. Thus, even when the outer region 322 has been folded, the thickness of the absorber 30 is restricted. The thickness of the absorber 30 is restricted, so that it is possible for a wearer to move more easily and the external appearance of the absorbent article 1 is also good. Furthermore, at the time of the wearing of the absorbent article 1, it is possible to prevent the extension units 320 from spreading outside in the widthwise direction W. Consequently, it is possible to improve comfortableness at the time of the wearing of the absorbent article 1 and to improve the absorption performance of bodily waste of the wearer.

In the present embodiment, along the longitudinal direction L of the absorber 30, the bending facilitation units 330 for facilitating the bending of the extension units 320 are formed. Specifically, the absorber 30 is provided with the first bending facilitation portion 331, the second bending facilitation portions 332, and the third bending facilitation portions 333. Accordingly, the first bending facilitation portion 331 is set as a base point, the vicinity of the center line CL of the absorber 30 bulges toward the side of a wearer, a part from the first bending facilitation portion 331 to the third bending facilitation portions 333 slacks toward a direction (a downward direction) separated from the wearer, and a part from the third bending facilitation portions 333 to the second bending facilitation portions 332 bulges toward the wearer (see FIG. 3 (b)).

Consequently, the absorber 30 is easily deformed in an approximate W shape when viewed from a sectional view thereof, and the extension unit 320 easily traces the movement of the wearer. As a consequence, the absorber 30 is prevented from being separated from the skin of the wearer, and fitting feeling to the wearer or comfortableness at the time of the wearing of the absorbent article 1 is improved. Furthermore, it also contributes to the prevention of side leakage of bodily waste.

In the present embodiment, the strand-shaped rubbers 33 are fixed to the absorber 30 in a stretched state along the longitudinal direction L. Accordingly, at the time of the wearing of the absorbent article 1, the tip portions 30E1 of the absorber 30 fit the skin of a wearer by the contraction of the strand-shaped rubbers 33. Consequently, it is possible to more reliably prevent side leakage of bodily waste of the wearer from occurring between the skin of the wearer and the crotch region S3.

In the present embodiment, in the state in which the extension units 320 have been folded toward the body unit 310, the absorber 30 is provided at the both side portions 30E thereof with a pair of leakage preventing units 40. Furthermore, the strand-shaped rubbers 41 constituting the leakage preventing unit 40 are fixed to the leakage preventing sheet 43 in a stretched state along the longitudinal direction L. Accordingly, at the time of the wearing of the absorbent article 1, the extension unit 320 easily rises up toward the skin of a wearer by the contraction of the leakage preventing units 40. Consequently, the absorbent article 1 easily fits (closely comes into contact with) the skin of the wearer, so that it is possible to reliably prevent side leakage of bodily waste of the wearer from occurring between the skin of the wearer and the crotch region S3.

In the present embodiment, the bonding end 40A of the leakage preventing unit 40 is positioned inside in the widthwise direction W of the absorber 30 with respect to the folding line IL. Accordingly, even when the extension units 320 are folded toward the body unit 310, since the leakage preventing unit 40 is not pulled toward the extension units 320, the leakage preventing unit 40 is allowed to be positioned outside in the widthwise direction with respect to the absorber 30. Furthermore, the free end 40B of the leakage preventing unit 40 is positioned outside in the widthwise direction W of the absorber 30 with respect to the folding line IL. That is, the leakage preventing unit 40 is reliably positioned outside in the widthwise direction with respect to the absorber 30. Consequently, it is possible to reliably perform the function of the leakage preventing unit 40 and to prevent side leakage.

Consequently, it is possible to prevent the interference of the leakage preventing unit 40 when the absorber 30 absorbs bodily waste of a wearer, and it is possible for the absorber 30 to directly absorb the bodily waste of the wearer. Thus, it is possible to more reliably improve the absorption performance of the bodily waste of the wearer while preventing the side leakage.

In the present embodiment, the width W320 of the absorber 30 in the extension unit 320 is wider than the width W311 of the absorber 30 in the wide portion 311. Consequently, it is possible to obtain sufficient absorption power by the extension unit 320 while ensuring good fitting feeling of the absorber 30 to a wearer.

Modification

The absorber core 31 according to the above-mentioned embodiment may be modified as follows.
In addition, the same reference numerals are used to designate the same element as the absorber core 31 according to the above-mentioned embodiment, and a difference will be mainly described.

First Modification

Figure 6:
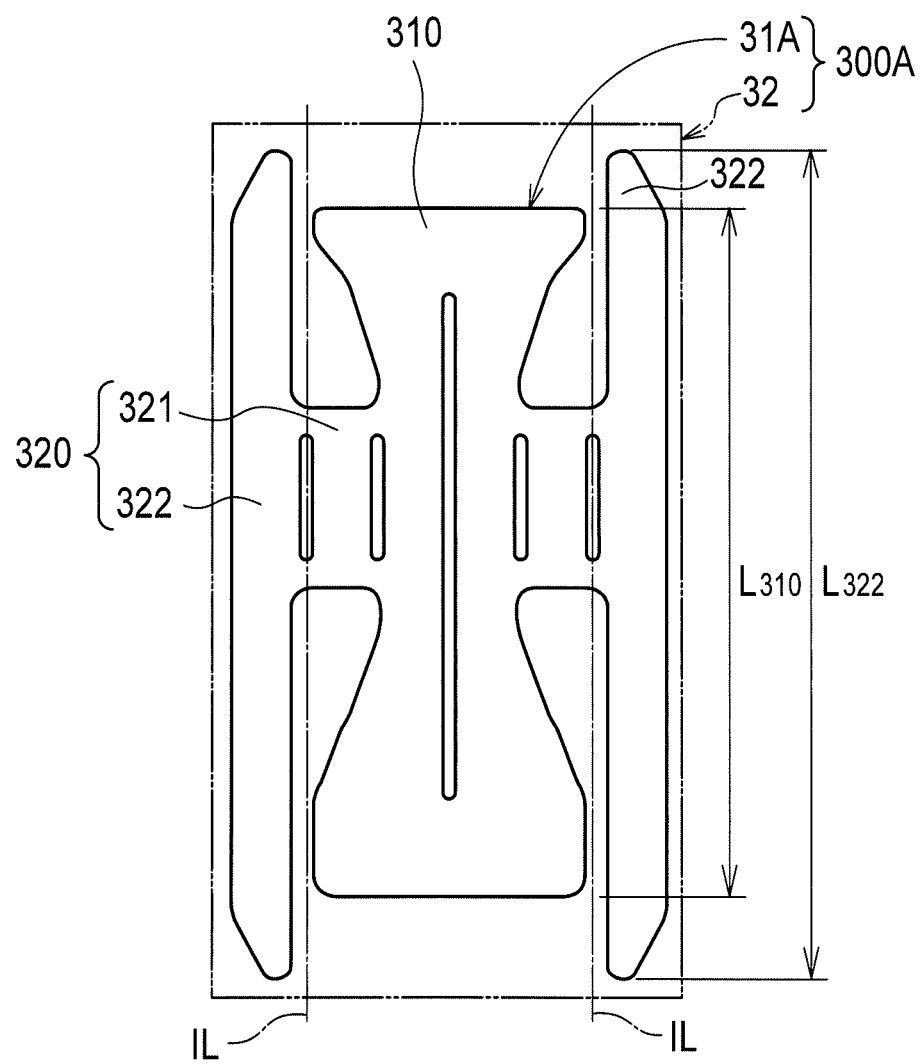
FIG. 6 is a plan view of an absorber 300A according to a first modification (before an outer region 322 is folded).

First of all, the structure of an absorber core 31A according to the first modification will be described with reference to the drawing.
FIG. 6 is a plan view of an absorber 300A according to the first modification (before the outer region 322 is folded).
In the above-mentioned absorber core 31, the maximum length L322 of the outer region 322 is shorter than the maximum length L310 of the body unit 310. On the other hand, in the first modification, the maximum length L322 of the outer region 322 is longer than the maximum length L310 of the body unit 310 as illustrated in FIG. 6.
In the first modification, the maximum length L322 of the outer region 322 is longer than the maximum length L310 of the body unit 310, resulting in an increase of an area where it is possible to diffuse bodily waste absorbed in the body unit 310 to the outer region 322. Consequently, it is possible to further improve the absorption performance of the bodily waste of a wearer.

Second Modification

Figure 7:
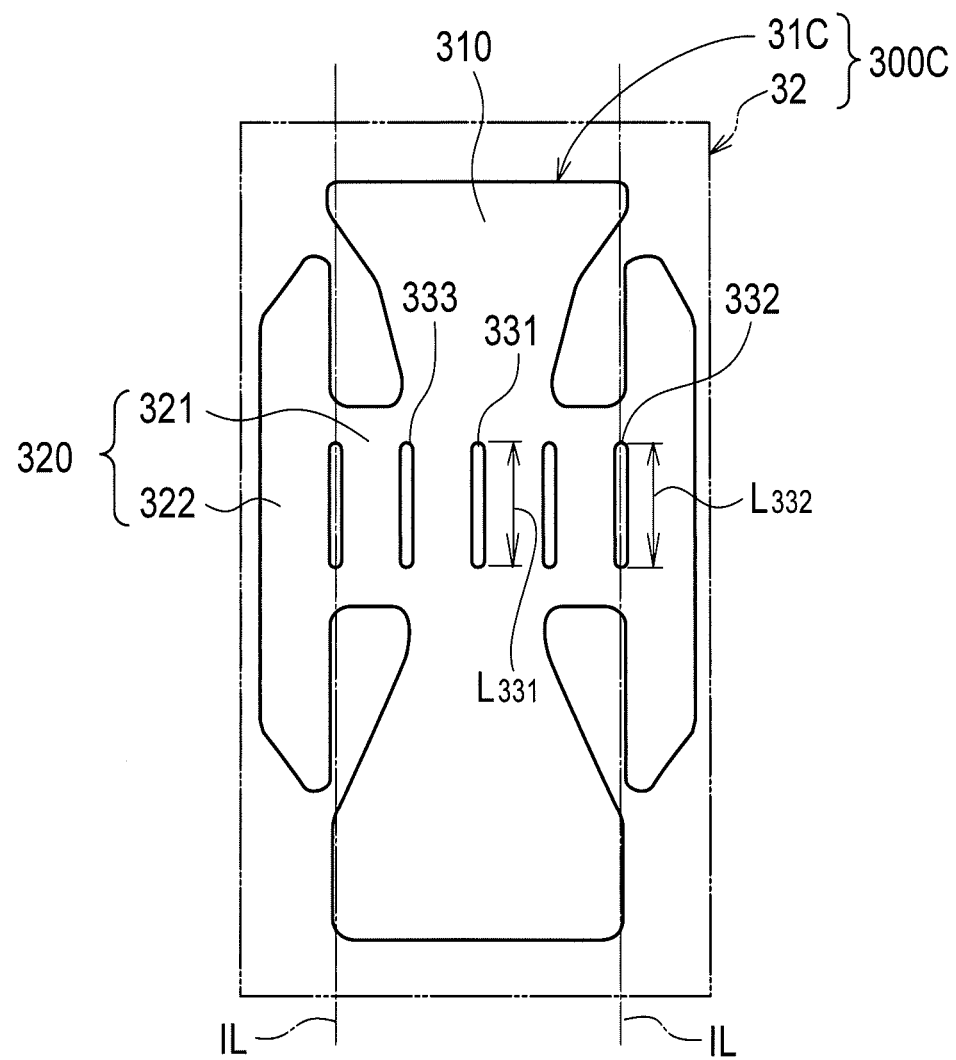
FIG. 7 is a plan view of an absorber 300C according to a second modification (before an outer region 322 is folded).

Next, the structure of an absorber core 31C according to the second modification will be described with reference to the drawing. FIG. 7 is a plan view of an absorber 300C according to the third modification (before the outer region 322 is folded).

In the above-mentioned absorber core 31, the first bending facilitation portion 331 extends from one wide portion 311 to the other wide portion 311. On the other hand, in the second modification, the length L331 of the first bending facilitation portion 331 is approximately the same as the length L332 of the second bending facilitation portion 332 as illustrated in FIG. 7.

In the second modification, the length L331 of the first bending facilitation portion 331 is approximately the same as the length L332 of the second bending facilitation portion 332, so that it is possible to increase a diffusion rate of the bodily waste of a wearer outside in the widthwise direction W as compared with a diffusion rate of the bodily waste of the wearer in the longitudinal direction L. Consequently, it is possible to design the length along the longitudinal direction L of the absorber 300C to be short.

Third Modification

Figure 8:
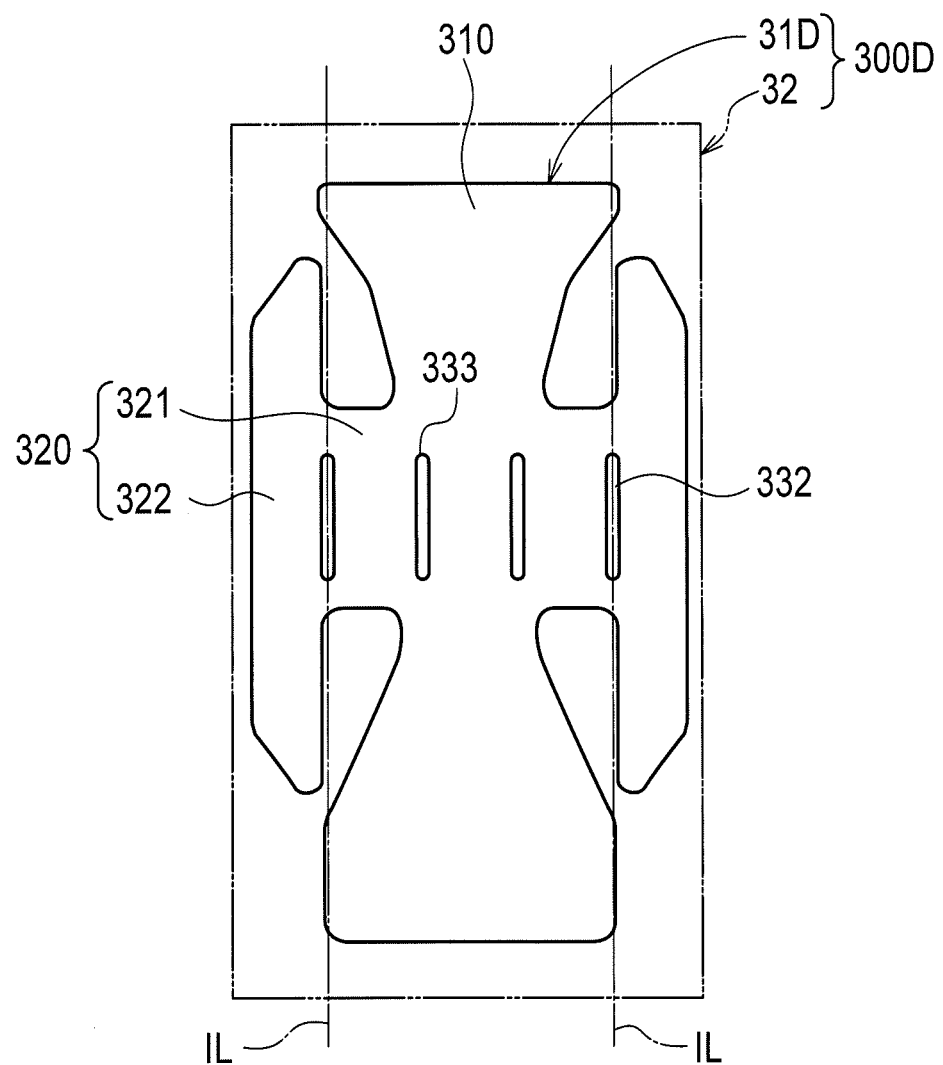
FIG. 8 is a plan view of an absorber 300D according to a third modification (before an outer region 322 is folded).

Next, the structure of an absorber core 31D according to the third modification will be described with reference to the drawing. FIG. 8 is a plan view of an absorber 300D according to the third modification (before the outer region 322 is folded).

In the above-mentioned absorber core 31, the bending facilitation unit 330 has the first bending facilitation portion 331, the second bending facilitation portions 332, and the third bending facilitation portions 333. On the other hand, in the third modification, the bending facilitation unit 330 has only the second bending facilitation portions 332 and the third bending facilitation portions 333, but does not have the first bending facilitation portion 331, as illustrated in FIG. 8.

In the third modification, the bending facilitation unit 330 has only the second bending facilitation portions 332 and the third bending facilitation portions 333, so that it is possible to easily deform the crotch region S3 to have an entirely curved state (that is, a cup shape), rather than an approximate W shape, when viewed from the sectional view of the absorber 30, and to form a space between the skin of a wearer and the crotch region S3. Consequently, even a lot of bodily waste has been excreted, the bodily waste stored in the space is gradually absorbed by the absorber 30, so that it is possible to prevent side leakage.

Fourth Modification

Figure 9:
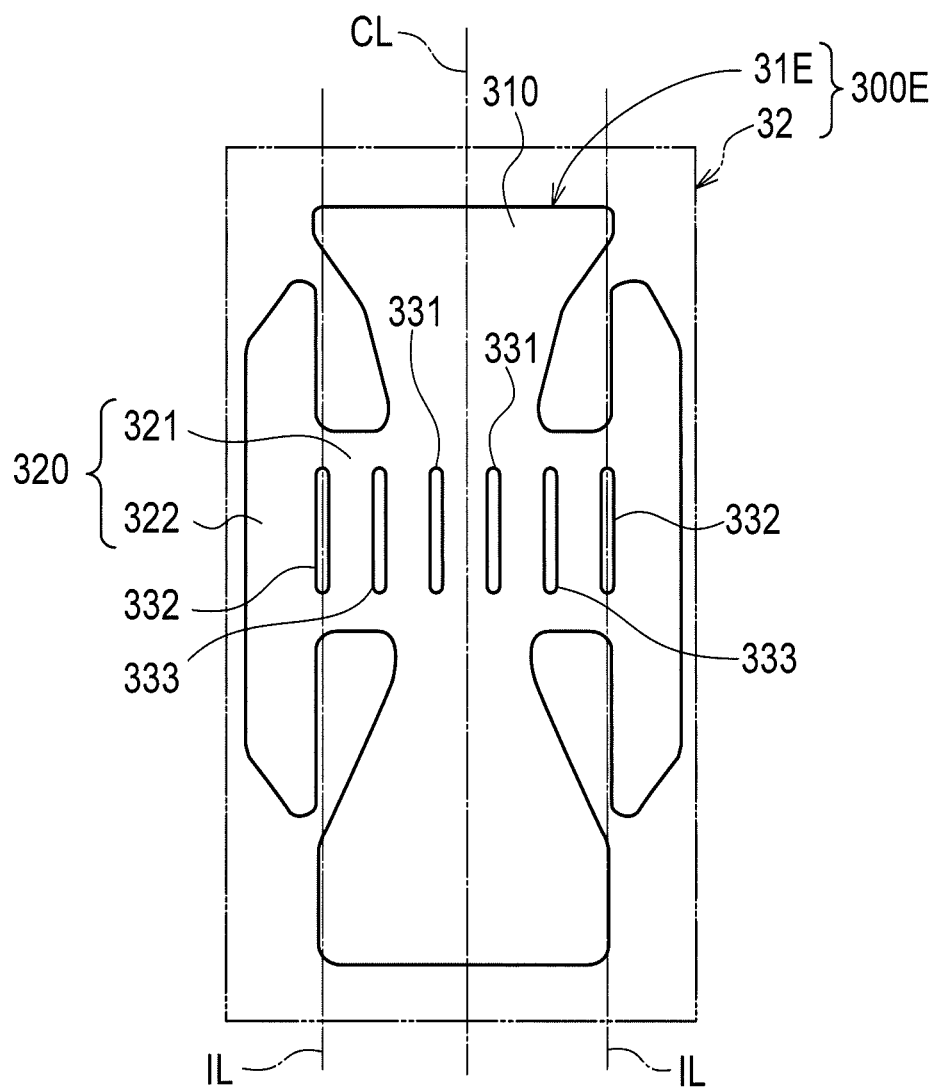
FIG. 9 is a plan view of an absorber 300E according to a fourth modification (before an outer region 322 is folded).

Next, the structure of an absorber core 31E according to the fourth modification will be described with reference to the drawing. FIG. 9 is a plan view of an absorber 300E according to the fourth modification (before the outer region 322 is folded).

In the above-mentioned absorber core 31, the first bending facilitation portion 331 is formed along the center line CL. On the other hand, in the fourth modification, the first bending facilitation portions 331 are line-symmetrically formed with respect to the center line CL as illustrated in FIG. 9.

In the fourth modification, the first bending facilitation portions 331 are line-symmetrically formed with respect to the center line CL, so that gaps (the vicinity of the center line CL) between the first bending facilitation portions 331 are directed to a direction (a downward direction) separated from the wearer. Furthermore, it is possible to regularly increase the number of bendings of the absorber 300E, so that it is possible to restrict a speed at which bodily waste of a wearer is diffused outside in the widthwise direction W, and to more reliably prevent side leakage.

Other Embodiments

As described above, the present invention is disclosed through the above embodiments. However, it should not be interpreted that the statements and drawings constituting a part of the present disclosure limit the present invention.
From this disclosure, various alternate embodiments, examples, and operation technology will become apparent to one skilled in the art.

For example, in the above-mentioned embodiments, the absorbent article 1 is a disposable diaper. However, the present invention is not limited thereto. It is a matter of course that it is sufficient if the absorbent article 1 is an article provided with the absorber 30 such as a sanitary napkin or a panty liner.

Furthermore, the absorbent article 1 or the manufacturing method of the absorbent article is not limited to the structures described in the embodiments. Other structures may also be employed. For example, the absorbent article 1 may have a dual layer structure of the topsheet 10 or the absorber 30. Furthermore, the absorbent article 1 may have a single layer structure of the backsheet 20. In this case, waist elastic members 3A and 3B or the like may be directly provided to the backsheet 20, and the backsheet 20 may be folded to allow the waist elastic members 3A and 3B to be in a sandwiched state, so that the waist elastic members 3A and 3B may be bonded with the backsheet 20. Furthermore, the absorbent article 1 may be not provided with the leakage preventing unit 40 or the like.

Furthermore, in the above embodiment, the folding line IL is positioned at the boundary between the inner region 321 and the outer region 322. However, the present invention is not limited thereto. For example, it is sufficient if the folding line IL is positioned between a part of the body unit 310, which has the narrowest width along the widthwise direction W of the absorber 30, and the outer edge 322a of the extension unit 320. That is, the extension unit 320 may be folded in the inner region 321 or in the outer region 322.

Furthermore, in the above embodiment, the length L1 from the outer edge 322a to the folding line IL is equal to or less than the length L2 from the center line CL to the folding line IL. However, the present invention is not limited thereto. For example, when the outer region 322 (the extension unit 320) is folded plural times, the length L1 from the outer edge 322a to the folding line IL may be longer than the length L2 from the center line CL to the folding line IL.

Furthermore, in the above embodiment, the interval W312A between the pair of foreside constricted portions 312A is wider than the interval W312B between the pair of backside constricted portions 312B. However, the present invention is not limited thereto. For example, the interval W312A may be equal to the interval W312B or may be narrower than the interval W312B.

Furthermore, in the above embodiment, the adhesive is coated on the corners of the covering members 32. However, the present invention is not limited thereto. For example, the adhesive may be coated on the covering members 32 corresponding to the whole of the outer region 322, or may be coated on the covering members 32 corresponding to only the both end portions 322b of the outer region 322. Furthermore, in the state in which the outer region 322 (the extension unit 320) has been folded toward the body unit 310, the topsheet 10 is bonded with the absorber 30, so that the outer region 322 may be held in a folded state. As described above, it is a matter of course that it is sufficient if the outer region 322 (the extension unit 320) can be held in the folded state.

Furthermore, in the above embodiment, the bending facilitation unit 330 has a slit shape which passes through the absorber core 31. However, the present invention is not limited thereto. The bending facilitation unit 330 may not pass through the absorber core 31. For example, the bending facilitation unit 330 is subject to an embossing process, so that the bending facilitation unit 330 may have the thinnest thickness in the absorber core 31. Moreover, it is sufficient if the bending facilitation unit 330 has any one of the first bending facilitation portion 331, the second bending facilitation portion 332, and the third bending facilitation portion 333.

Furthermore, in the above embodiment, the absorber 30 is provided at the tip portion 30E1 thereof with the pair of strand-shaped rubbers 33. However, the present invention is not limited thereto. For example, the pair of strand-shaped rubbers 33 may not be provided.

Furthermore, in the above embodiment, the bonding end 40A is provided inside of the folding line IL in the widthwise direction W of the absorber 30. However, the present invention is not limited thereto. For example, the bonding end 40A may be provided on the folding line IL or provided outside of the folding line IL in the widthwise direction W of the absorber 30.

Furthermore, in the above embodiment, the free end 40B is provided outside of the folding line IL in the widthwise direction W of the absorber 30 in the state in which the extension unit 320 has been folded toward the body unit 310. However, the present invention is not limited thereto. For example, the free end 40B may be provided on the folding line IL or provided inside of the folding line IL in the widthwise direction W of the absorber 30.

Furthermore, the leakage preventing unit 40 may not be provided in the absorbent article 1. That is, a planar sheet (a planar gather structure) or the like, separately from the leakage preventing unit 40, but having the bonding end 40A and the free end 40B, may be provided instead of the leakage preventing unit 40.

As described above, needless to say, the present invention includes various embodiments and the like not described here. Therefore, the technical range of the present invention is to be defined only by the inventive specific matter according to the adequate claims from the above description.

The entire contents of Japanese Patent Application No. 2009-298972 (filed on Dec. 28, 2009) are incorporated in the present specification by reference.

INDUSTRIAL APPLICABILITY

According to the present invention, it is possible to provide an absorbent article capable of reliably preventing side leakage of bodily waste while ensuring good fitting feeling to a wearer.

REFERENCE SIGNS LIST

1 . . . absorbent article, 3A, 5A . . . waist elastic member, 10 . . . topsheet, 20 . . . backsheet, 30 . . . absorber, 30E . . . both side portion, 30E1 . . . both side edges, 31, 31A, 31C, 31D, 31E . . . absorber core, 32 . . . covering member, 33 . . . strand-shaped rubber, 40 . . . leakage preventing unit, 40A . . . bonding end, 40B . . . free end, 41 . . . strand-shaped rubber, 42 . . . leakage preventing film, 43 . . . leakage preventing sheet, 70A . . . foreside waist sheet, 70B . . . backside waist sheet, 100 . . . product continuous body, 110 . . . topsheet web, 132 . . . covering member web, 132A . . . both end portions, 133 . . . rubber continuous body, 140 . . . leakage preventing unit web, 220 . . . exterior topsheet, 230 . . . exterior sheet, 231 . . . foreside exterior sheet, 232 . . . backside exterior sheet, 233 . . . crotch exterior sheet, 233A . . . crotch inner sheet, 233B . . . crotch outer layer sheet, 233C . . . crotch sheet, 234 . . . front waistline exterior sheet, 235 . . . rear waistline exterior sheet, 300A, 300C to 300E . . . absorber, 310 . . . body unit, 311 . . . wide portion, 312A, 312B . . . constricted portion, 320 . . . extension unit, 321 . . . inner region, 322 . . . outer region, 322a . . . outer edge, 322b . . . both end portions, 323 . . . cutout portion, 330 . . . bending facilitation unit, 331 . . . first bending facilitation portion, 332 . . . second bending facilitation portion, 333 . . . third bending facilitation portion

The invention claimed is:

1. An absorbent article having a longitudinal direction and a widthwise direction crossing the longitudinal direction, said absorbent article comprising:
 a topsheet provided at a side configured to come into contact with a skin of a wearer;
 a backsheet provided at a side configured to be separated from the wearer's skin; and
 an absorber provided between the topsheet and the backsheet, wherein both side portions of the absorber in the widthwise direction are folded,
 wherein the absorber comprises:
 a body unit having a constricted portion constricted inwardly in the widthwise direction when viewed from a plan view of the absorber; and
 a pair of extension units extending from the body unit outwardly in the widthwise direction in a state in which the both side portions have been unfolded,
 wherein the constricted portion is formed in a center region in the longitudinal direction, and
 wherein each of the extension units comprises:
 an inner region provided at the constricted portion and continuous to the body unit; and
 an outer region continuous to the inner region and positioned outside of the inner region in the widthwise direction,
 wherein the outer region is folded toward the inner region at a side of the topsheet, and a length of the inner region along the longitudinal direction is shorter than a length of the outer region along the longitudinal direction, and
 wherein a width of the absorber from an outer edge of one of the extension units to an outer edge of the other extension unit is wider than a width of the absorber in an end portion in the longitudinal direction in a state in which the both side portions have been unfolded.

2. The absorbent article according to claim 1, wherein the outer region is folded along a folding line extending in the longitudinal direction, and
 a length along the widthwise direction from an outer edge of the outer region to the folding line is equal to or less than a length along the widthwise direction from a center line of the absorber to the folding line, the center line passing through a center of the body unit in the widthwise direction.

3. The absorbent article according to claim 1, wherein the absorber is covered with a sheet-shaped member,
 the outer region is folded together with the sheet-shaped member, and
 at least a part of the sheet-shaped member positioned outside of the outer region in the longitudinal direction of the absorber is bonded with the body unit.

4. The absorbent article according to claim 2, wherein the absorber further comprises a bending facilitation unit configured to allow the extension unit to be bent along the folding line or a straight line parallel to the folding line.

5. The absorbent article according to claim 4, wherein the bending facilitation unit comprises a bending facilitation portion formed along the center line and positioned corresponding to the extension unit in the longitudinal direction.

6. The absorbent article according to claim 4, wherein the bending facilitation unit is a slit formed in the absorber.

7. The absorbent article according to claim 4,
wherein the bending facilitation unit comprises:
   a first bending facilitation portion formed along the center line; and
   a second bending facilitation portion positioned outside the first bending facilitation portion in the widthwise direction and extending along the longitudinal direction, and
wherein the first and second bending facilitation portions are positioned corresponding to the extension units in the longitudinal direction.

8. The absorbent article according to claim 1, wherein
each of the extension units further comprises a tip portion directed at the other extension unit in the widthwise direction, the tip portions including a pair of elastic members extending along the longitudinal direction, and the elastic members are fixed to the absorber in a stretched state along the longitudinal direction.

9. The absorbent article according to claim 1,
wherein in a state in which the extension units have been folded toward the body unit, a pair of leakage preventing units formed along the longitudinal direction is provided at the both side portions of the absorber in the widthwise direction, and
wherein each of the leakage preventing units comprises:
   a leakage preventing elastic member extending along the longitudinal direction; and
   a sheet surrounding the leakage preventing elastic member,
wherein the leakage preventing elastic member is fixed to the sheet in a stretched state in the longitudinal direction.

10. The absorbent article according to claim 9,
wherein the leakage preventing unit comprises:
   a bonding end which is bonded with the absorber; and
   a free end opposite to the bonding end in the widthwise direction,
wherein the bonding end is positioned inside of the folding line in the widthwise direction, and the free end is positioned outside of the folding line in the widthwise direction.

* * * * *